United States Patent
Sliwa, Jr. et al.

(10) Patent No.: US 6,511,427 B1
(45) Date of Patent: Jan. 28, 2003

(54) SYSTEM AND METHOD FOR ASSESSING BODY-TISSUE PROPERTIES USING A MEDICAL ULTRASOUND TRANSDUCER PROBE WITH A BODY-TISSUE PARAMETER MEASUREMENT MECHANISM

(75) Inventors: John W. Sliwa, Jr., Los Altos, CA (US); Vaughn R. Marian, Saratoga, CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/522,985

(22) Filed: Mar. 10, 2000

(51) Int. Cl.⁷ .................................................. A61B 8/00
(52) U.S. Cl. ........................................ 600/438; 600/459
(58) Field of Search ................................. 600/459, 463, 600/372, 442, 438, 547, 461, 485, 587, 443, 439

(56) References Cited

U.S. PATENT DOCUMENTS

| | | | |
|---|---|---|---|
| 4,291,708 A | * | 9/1981 | Frei et al. .................... 600/547 |
| 4,423,738 A | * | 1/1984 | Newgard .................... 600/485 |
| 5,099,848 A | | 3/1992 | Parker et al. |
| 5,107,837 A | | 4/1992 | Ophir et al. |
| 5,115,808 A | | 5/1992 | Popovic et al. |
| 5,178,147 A | | 1/1993 | Ophir et al. |
| 5,278,776 A | | 1/1994 | Fisher et al. |
| 5,293,870 A | | 3/1994 | Ophir et al. |
| 5,524,636 A | | 6/1996 | Sarvazyan et al. |
| 5,606,971 A | * | 3/1997 | Sarvazyan ................... 600/438 |
| 5,749,364 A | * | 5/1998 | Sliwa, Jr. et al. ............ 600/438 |
| 5,797,849 A | * | 8/1998 | Vesely et al. ................ 600/461 |
| 5,876,345 A | | 3/1999 | Eaton et al. |
| 5,919,139 A | * | 7/1999 | Lin ............................. 600/443 |
| 6,014,473 A | | 1/2000 | Hossack et al. |
| 6,083,170 A | * | 7/2000 | Ben-Haim ................... 600/462 |

OTHER PUBLICATIONS

Peter Niemczyk; Correlation of Mechanical Imaging and Histopathology of Radical Prostatectomy Specimens: A Pilot Study for Detecting Prostrate Cancer; Sep. 1998; pp. 1–5.

* cited by examiner

Primary Examiner—Marvin M. Lateef
Assistant Examiner—Ruby Jain

(57) ABSTRACT

A system and method for diagnostic ultrasound imaging with a probe combining one or more ultrasound imaging transducer elements and a body-tissue parameter measurement mechanism to detect body-tissue properties. At least one ultrasound transducer element provides an ultrasound image field of view of at least a portion of the body-tissue being measured by the parameter measurement mechanism. The parameter measurement mechanism is typically a mechanically or electrically operated mechanism attached to the probe near at least one ultrasound transducer element in order to combine information from the body-tissue parameter measurement mechanism and ultrasound transducer element for easier identification of abnormal body-tissue properties (e.g., tumors, dead, or diseased body-tissue).

51 Claims, 6 Drawing Sheets

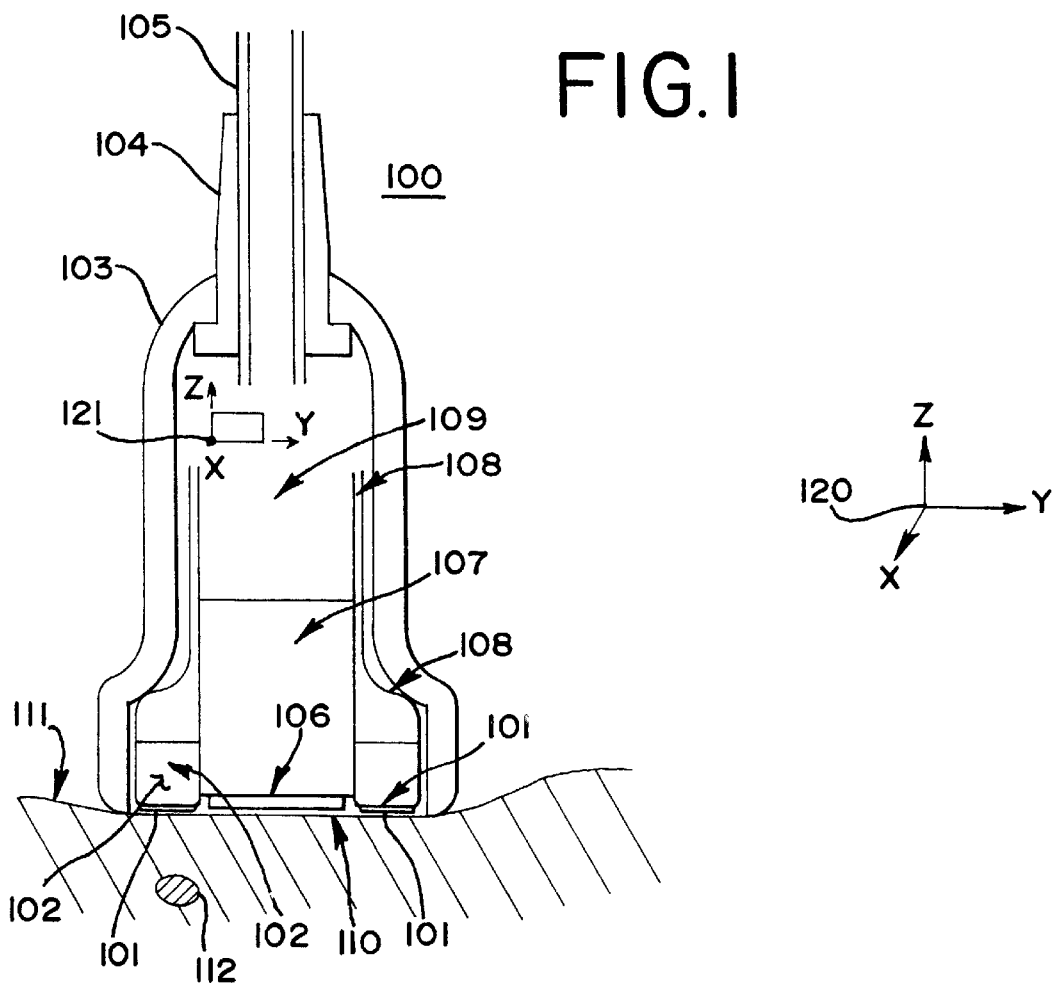
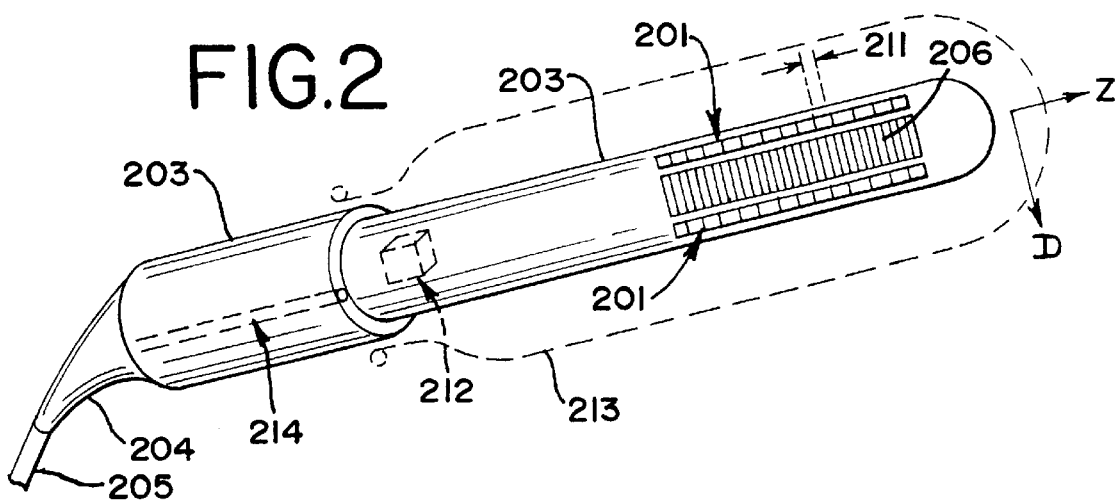

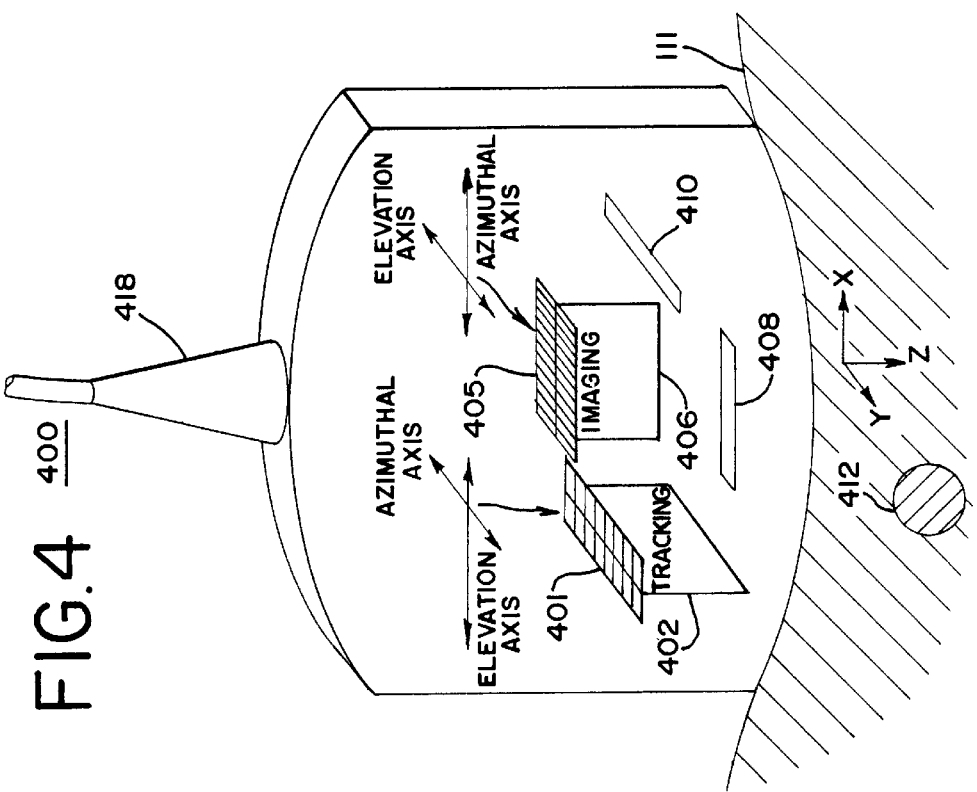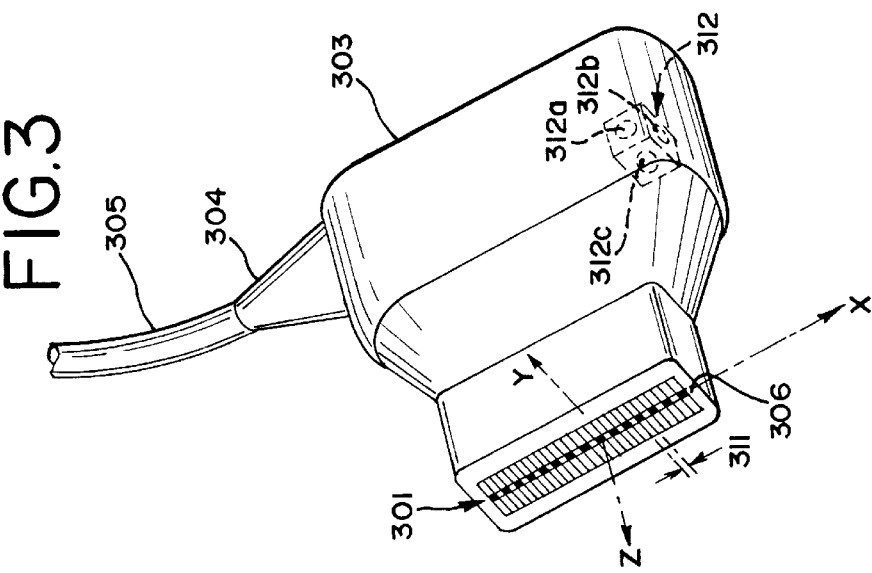

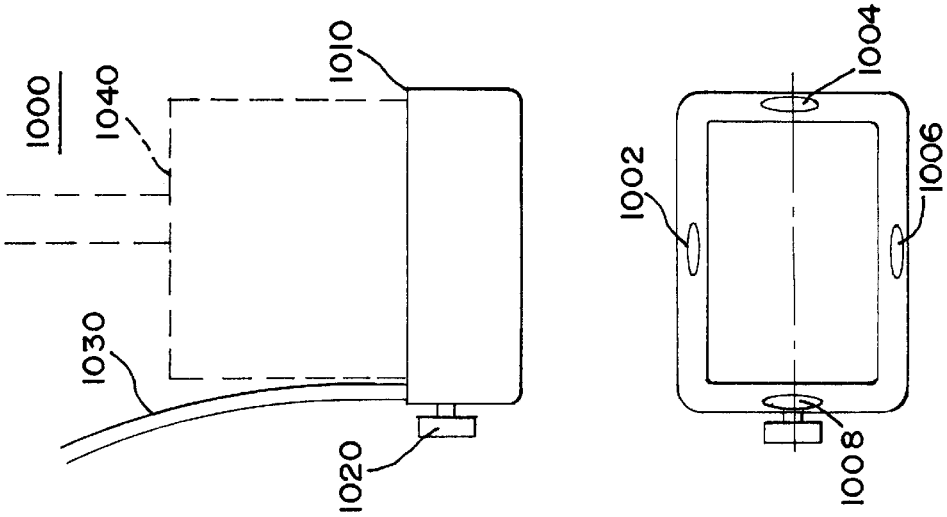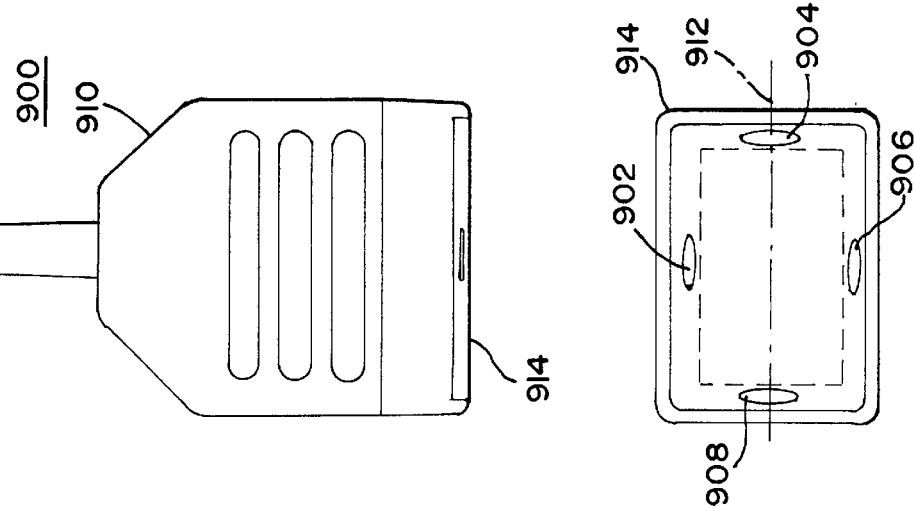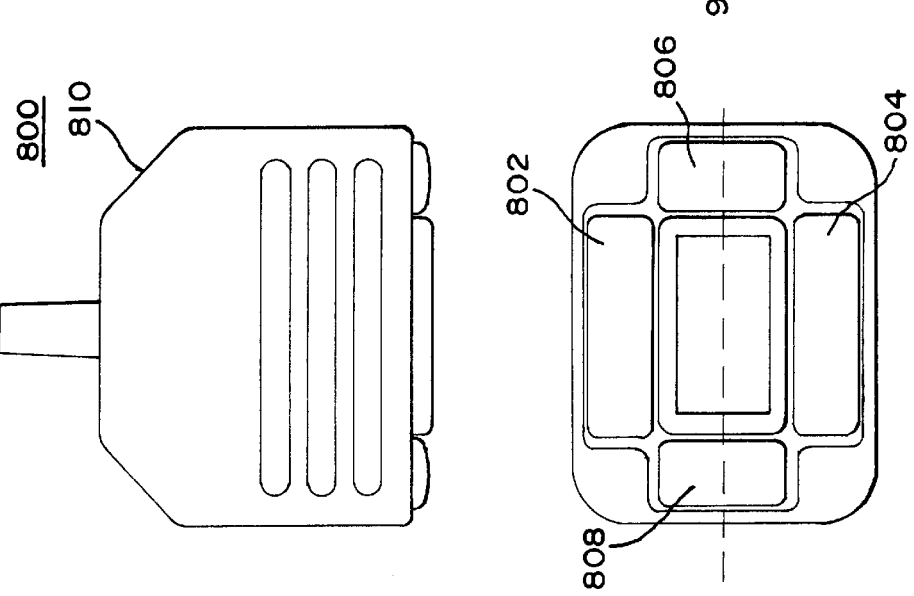

SYSTEM AND METHOD FOR ASSESSING BODY-TISSUE PROPERTIES USING A MEDICAL ULTRASOUND TRANSDUCER PROBE WITH A BODY-TISSUE PARAMETER MEASUREMENT MECHANISM

BACKGROUND OF THE INVENTION

1. Field of Invention

This invention relates generally to an improvement in diagnostic medical ultrasound imaging, and more specifically to a system and method for integrating a diagnostic medical ultrasound transducer probe with a body-tissue parameter measurement mechanism for examination of body-tissue, in conjunction with diagnostic ultrasound imaging.

2. Description of the Prior Art

There is growing interest in 2-D and 3-D ultrasound imaging for diagnostic medical applications. Commonly available ultrasound systems for medical applications include ultrasound imaging probes with one or more one-dimensional (1-D) ultrasound transducer arrays for obtaining 2-D images of body-tissue. Such ultrasound imaging probes are designed exclusively for passive ultrasound imaging. Subtle differences in ultrasound images of body-tissue are used to detect the presence of undesirable body-tissue, such as tumors. Sometimes the acoustic impedance contrast between healthy and undesirable body-tissue is too small for detection by ultrasound imaging alone.

Alternatively, undesirable body-tissue can frequently be detected by manual palpation, such as by physical examination of breast or prostate tissue for hard lumps or lesions. Unfortunately, manual palpation is not very quantitative nor repeatable, and the feel of a tumor varies greatly with its depth from the body-tissue surface. Thus, the sensitivity of detecting undesirable body-tissue by the nonquantitative manual palpation of body-tissue alone is limited.

In order to solve these palpation sensitivity and quantification problems, there has been discussion of using force-sensing mechanisms for breast and rectal prostate exams. For example, the use of a Tekscan™ 2-D planar piezoresistive force sensing array for prostate exams is discussed in an article entitled "Correlation of Mechanical Imaging and Histopathology of Radical Prostatectomy Specimens: A Pilot Study for Detecting Prostate Cancer," by P. Niemczyk et al., Journal of Urology, Vol. 160, pp. 1–5, September 1998. Furthermore, a BreastCheck™ handheld mapping device with a pressure-sensing array for detection of breast nodules, made by the Assurance Medical Division of UroMed Corporation, located in Hopkinton, Mass., is undergoing clinical testing.

But there has been no disclosure of body-tissue palpation or other parameter measurement mechanisms integrated within or attached to ultrasound imaging probes for body-tissue parameter measurement in combination with 2-D or 3-D ultrasound imaging. Complementary examination of body-tissue by sequential (or simultaneous) use of ultrasound imaging and body-tissue palpation or other parameter measurement could provide more sensitivity in detecting undesirable body-tissue. Furthermore, the above references do not address the more difficult problem of sensing deeper tumors using body-tissue surface force-sensing mechanisms.

What is needed is a system, method, and probe to obtain 2-D or 3-D ultrasound images of body-tissues in combination with coregistered or overlaid software or hardware controlled body-tissue parameter measurements. The ultrasound system and method should be relatively low in cost and permit efficient examination and identification of tumors and other undesirable body-tissues. Ideally, body-tissue parameter measurement should allow for the application of static or dynamic body-tissue loading at any point on or in the body-tissue surface or depth, as well as the direct sensing of body-tissue surface parameters.

SUMMARY OF THE INVENTION

One object of the present invention is to provide a system, method, and probe to obtain 2-D or 3-D ultrasound images of body-tissues in combination with software or hardware controlled body-tissue parameter measurement. For 3-D imaging using principal imaging and secondary motion-tracking transducers, the principal and secondary imaging information needs to be provided concurrently, such that the secondary imaging information can be used to estimate the movement of the transducer probe and/or the body-tissue between respective image data frames.

Another object of the invention is to provide a relatively low cost ultrasound system, method, and probe to permit efficient examination and identification of tumors and other undesirable body-tissues.

The invention is directed to a medical diagnostic ultrasound probe, including one or more ultrasound imaging transducer elements and a body-tissue parameter measurement mechanism.

These and other objects and advantages of the invention will become apparent to those skilled in the art from the following detailed description of the invention and the accompanying drawings.

BRIEF DESCRIPTION OF THE DRAWINGS

FIG. 1 is a sectional view of an ultrasound imaging probe, including a peripheral pressure-mapping sensing mechanism for providing contact-pressure information and diagnostic ultrasound information.

FIG. 2 shows a partial side cross-section of another preferred embodiment of the invention.

FIG. 3 shows a perspective view of another preferred embodiment of the invention.

FIG. 4 is a perspective schematic view of one preferred probe configuration of a principal transducer array, a secondary motion-tracking transducer array, and a body-tissue palpation system.

FIG. 8 is a side and bottom view of an ultrasound transducer probe with four tissue displacing mechanisms for body-tissue palpation.

FIG. 9 is a side and bottom view of an ultrasound transducer probe with four electrodes for electrical stimulation of body-tissue displacement.

FIG. 10 is a side (profile) and bottom view of an ultrasound transducer probe accessory with four electrodes for electrically stimulating body-tissue displacement.

DETAILED DESCRIPTION OF PREFERRED EMBODIMENTS

Figure 5:
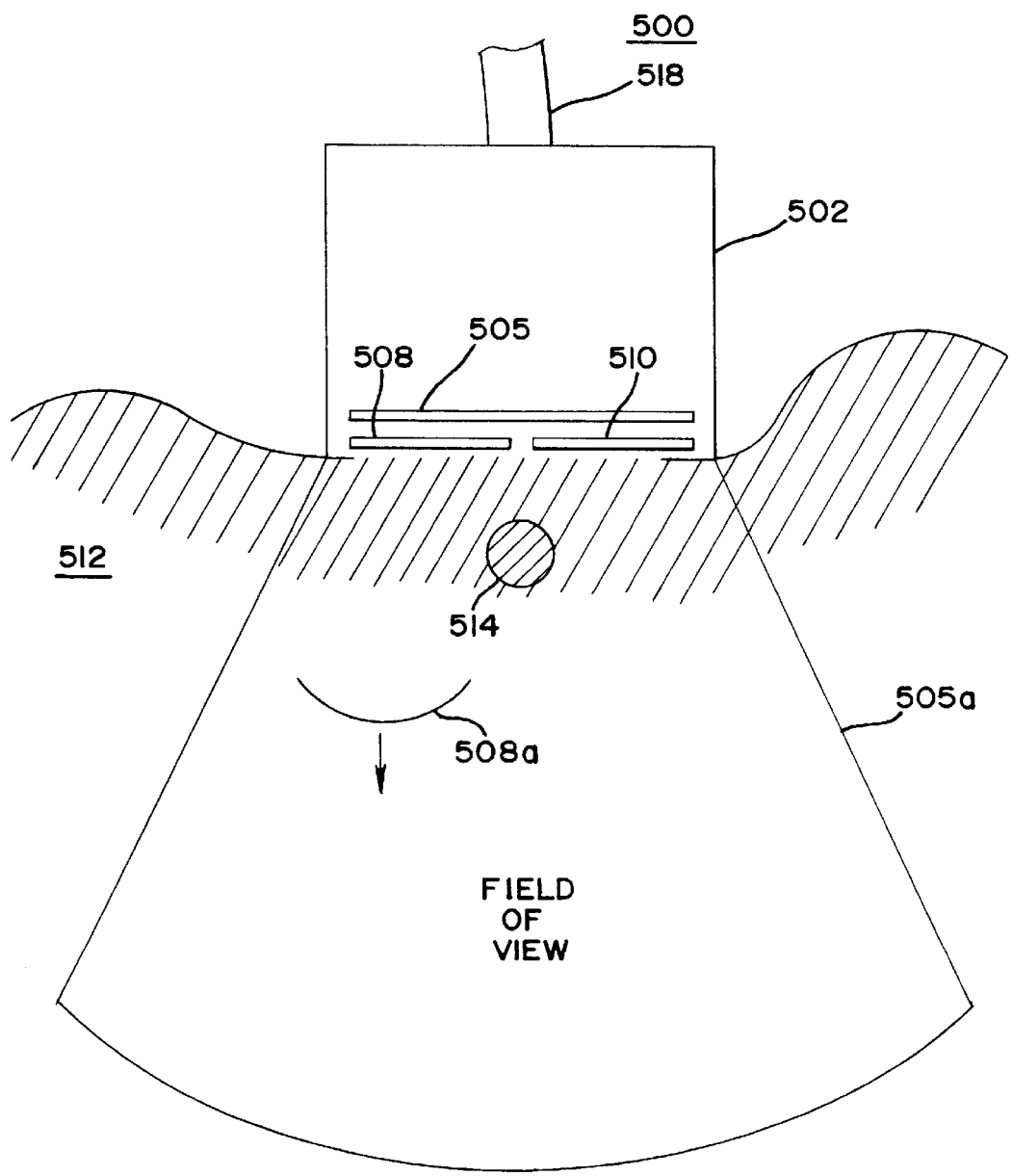
FIG. 5 is a side view of one preferred construction of a transducer probe contacting body-tissue.

A first embodiment is directed to an ultrasound imaging probe with one or more ultrasound imaging transducer elements for ultrasound imaging of body-tissue, and an integrated body-tissue parameter measurement mechanism for measuring a body-tissue parameter on a point-by-point basis or on a distributed, regional basis. At least one point of measured body-tissue is in the field of view of at least one ultrasound imaging transducer element. A body-tissue parameter is a measured or computed characteristic of body-tissue within the field of view of the ultrasound imaging transducer element, and not only a surface characteristic of body-tissue. One such known parameter is shear-modulus.

In a second embodiment, the invention is directed to an ultrasound imaging probe with one or more ultrasound imaging transducer elements for ultrasound imaging of body-tissue, and an integrated mechanical mechanism for displacing body-tissue or applying pressure in a controlled manner within the field of view of at least one ultrasound imaging transducer element.

Positional information may be derived from multiple transducer array ultrasound imaging, as described in co-pending U.S. Pat. No. 6,014,473, entitled "Multiple Ultrasound Image Registration System, Method and Transducer," which is assigned to the assignee of the present invention and hereby incorporated herein by reference. In preferred embodiments, a principal imaging transducer array provides an ultrasound image, and at least one secondary imaging transducer array selectively provides additional ultrasound data which are used, at least in part, to deduce transducer position in 3D spatial coordinates.

The invention is typically and preferably implemented with phased (steered beam) ultrasound arrays placed in proximity to one or more body-tissue manipulation or palpation tools. The ultrasound principal imaging and secondary tracking transducer arrays need not be the same, but it would simplify the system configuration if the transducer arrays were the same.

In a typical embodiment, the ultrasound principal imaging transducer array may comprise 64 to 256 elements in an azimuthal line, with a 12 Megahertz (MHz) center frequency on a 0.1 to 0.2 millimeters (mm) element-to-element pitch. The elements are typically between 2 and 4 mm in elevation dimension (i.e., a dimension perpendicular to the array or azimuthal axis). The ultrasound secondary transducer array typically comprises 16 to 128 elements, ideally having the same center frequency, pitch, and elevation dimension as the principal imaging transducer array. One preferred embodiment of the invention includes a principal imaging transducer array having 128 elements with a 12 MHz center frequency on a 0.1 mm element-to-element pitch, and a 2 mm elevation dimension, and a secondary imaging transducer array, with 128 elements with the same frequency, pitch, and elevation dimension as the secondary array. The scan format of the arrays may be of any type (e.g., linear, sector, Vector® wide view, curvilinear, curved Vectorg wide view, or radial). In a preferred embodiment, the maximum dimension of the probe contact area is less than 150 mm. The azimuthal length of a preferred embodiment of the probe is between 15 to 100 millimeters (mm).

A first embodiment of the invention is directed to a diagnostic medical ultrasound probe with one or more ultrasound imaging transducer elements and a mechanism comprised of one or more force or pressure sensing devices or pressure applying devices. Pressure includes static pressure and/or dynamic (time-varying) pressure.

One diagnostic medical application is body-tissue imaging for the detection of tumors or lesions. Another surgical application for the invention is body-tissue imaging for the assessment of the prospective removal of distinct types of body-tissues, such as removing burned skin and body-tissue for performing a satisfactory skin graft. The invention can also be applied to probes for other applications, such as vaginal probes and intra-luminal probes, and for application to determining the mechanical properties of muscles, tendons, and skin layers.

FIG. 1 is a sectional view 100 of an ultrasound imaging probe 103 including a peripheral pressure-mapping sensing mechanism 101 for providing both pressure information and diagnostic ultrasound imaging information. Ultrasound imaging probe 103 includes pressure-sensing or pressure applying mechanisms 101, pressure-sensing or pressure-applying mechanism backers 102, strain relief 104, connecting cable 105, and protective rubber window or membrane 110. The probe 103 is applied and acoustically coupled to body-tissue 111. Body-tissue 111 contains a tumor or hard nodule 112 to be detected. Pressure-mapping sensing mechanisms or pressure application mechanisms 101 (or a combined mechanism) mounted on dedicated backers 102 are arranged peripherally to PZT imaging transducer array 106 mounted on attenuating backing block 107. At least one flexible circuit or wiring bundle 108 connects PZT imaging transducer array 106 and pressure-mapping sensing mechanisms 101 to coaxial electrical termination region 109 in the interior of ultrasound imaging probe 103. Also shown are coordinate system 120 and spatial position sensing mechanism 121, capable of reporting the spatial position of imaging probe 103 to the ultrasound system (not shown). The face of the PZT imaging transducer array 106 is typically rectangular. Pressure-sensing mechanisms 101 are arranged on the periphery of PZT imaging transducer array 106 in order to be in physical or mechanical contact with body-tissue 111, across the full azimuthal and elevational dimensions of PZT imaging transducer array 106 and pressure-sensing mechanisms 101.

The device of FIG. 1 may be used to provide an ultrasound image as well as a passive pressure map of the tissue surface correlated spatially with the image. In such an example, for example, the tumor 112 would show up as a hard (higher contact pressure) spot. The device of FIG. 1 may also be used in an active mode wherein pressure mechanism 101 emits dynamic pressure waves whose effects on tissue are assessed in the correlated ultrasound image.

A second embodiment of the invention is directed to a diagnostic medical ultrasound probe with one or more ultrasound imaging transducer elements and a body-tissue mechanical displacement mechanism comprised of one or more mechanical actuators or voice coils. The body-tissue mechanical displacement mechanism is preferably comprised of separate electromechanical elements or tools, such as solenoids or voice coils, controlled in amplitude of body-tissue displacement, frequency of body-tissue displacement, and phase of body-tissue displacement. At least part of the body-tissue displacement occurs in the field of view of at least one ultrasound imaging transducer element. Thus, the effects of the transmitted pressure waves on the ultrasound image of a particular portion of tissue may be seen or even mapped.

In one preferred embodiment, the body-tissue properties are determined from the combination of body-tissue distortions acoustically imaged with PZT imaging transducer array 106 and applied forces measured by pressure-mapping sensing mechanisms 101, which may report at least one of normal, torsional, rotational, compressional, and shear forces being applied to body-tissue 111 causing said distortions. 3-D imaging is available by utilizing a spatial position sensing mechanism 121, such as a magnetic positioning sensor, capable of assigning a spatial address to each frame of ultrasound and pressure information. Such spatial positioning for 3-D imaging may also be provided by the aforementioned image-based motion tracking method described in U.S. Pat. No. 6,014,473. A pressure map or audible tone can be displayed or sounded in association with an ultrasound image in order to control the applied forces and to display spatial and/or temporal relationships between the ultrasound images and forces applied to the body-tissue verses time and verses position. For example, the ultrasound display can show both an ultrasound image and a graph of transducer probe contact force to tissue along the azimuthal dimension Y of FIG. 1, or it can show computed applied dynamic pressures applied at depth from information concerning the operation of pressurization mechanisms 101. Thus, system computations may quantify the observed body-tissue displacements (due to one or both of manual probe contact and/or probe pressurization via mechanisms 101), and observed body-tissue loading (pressure) map and colorize regions of the ultrasound image in relation to computed stiffness or computed dynamic deformability.

In another preferred embodiment, spatial pressure maps of a region of body-tissue are displayed with ultrasound images of the region of body-tissue. These may include body-tissue surface pressures as well as deduced or modeled loading at depth. Preferably, a display monitor displays the spatial pressure maps and the ultrasound images taken from the same field of view by an integrated probe. The ultrasound system may also compute or infer applied pressures (or forces) at depth using forces known at the skin line from passive sensing and/or computer propagation patterns of dynamic forces applied at the skin line. Such cooperative presentation of imagery and pressure/property maps may be, for example, via techniques such as interleaving or combining both types of signals to present one combined image.

The pressure-sensing (or application) mechanisms 101, if located on the periphery of the PZT (or another piezoelectric material) imaging transducer array 106, may be fabricated from any force-transducing material commonly known in the art (e.g., Polyvinyldienefluoride piezofilms, PZT, or other piezoelectric or piezoactive materials). The pressure mechanisms 101 may be of a matrix design and may have tightly spaced pixels (as tightly spaced as manufacturable) or loosely spaced pixels in order to allow beamforming of the pressurization at depth. The pressure mechanisms 101 may consist of single rows of pixels or multiple rows of electrically independent or electrically common pixels. Typically, force-sensing devices 101 use either capacitance or resistance principles. In either case, the sensing mechanism core consists of a material whose capacitance, resistance, or optical property changes with applied forces in a predetermined manner. Alternatively, newer sensing mechanisms comprised of braided optical fibers can be used. The optical conductivity of the fiber array is affected by contact pressure or bending. Sharing of piezoelectric material between ultrasound imaging and pressure-sensing may be possible. Additionally, force-imposing mechanisms 101 can comprise a piezo-material, or a voice-coil or electromechanical, or pneumatic vibrator mechanism.

Preferably, the electromechanical embodiments described above use solenoids or voice coils with a stroke of less than a centimeter, available from Magnetic Sensor Systems, located in Van Nuys, Calif.; Magnetec Corporation, located in Bloomfield, Conn.; or Magnet-Scholtz of America, located in Westmont, Ill.

A variation of this "sharing" embodiment includes pressure-sensing or pressure- application mechanisms 101 placed over or under the face of the PZT imaging transducer array 106. This offers the advantage of reducing the lateral dimensions of the face of the ultrasound imaging probe. A potential disadvantage of this variation is that the pressure mechanisms 101 are now in the acoustic path of the PZT imaging transducer array 106. For this embodiment, the ultrasound imaging transducer array may comprise a material (e.g., Polyvinyldienefluoride (PVDF) or another piezoelectric polymeric material) capable of both receiving ultrasound images and simultaneously or intermittently sensing contact pressure on body-tissue 111. PVDF is capable of excellent ultrasound image reception, as well as excellent low frequency/DC force or pressure-sensing. However, PVDF is not a very good ultrasound transmitter, so a separate transmitter may be desirable for palpating deeper depths. An overlying pressure-sensing mechanism may also be acoustically beneficial to the ultrasound imaging array as, for example, in the case wherein a pressure-sensing PVDF layer doubles as an acoustic matching layer for PZT imaging transducer array 106.

In this manner, PZT imaging transducer array 106 primarily comprises a conventional and efficient piezoelectric ceramic (e.g., PZT5H material). Polymeric-based acoustic matching layers are widely used in the ultrasound industry, so one may be made piezoactive. Alternatively, glass-based matching layers are widely used in the ultrasound industry and optical fiber based pressure-sensing mechanisms may also be integrated into matching layers.

Preferably, the membrane or window 110 shown in FIG. 1 is thin so as to not smooth-over or hide pressure peaks originating from underlying tumors 112.

Preferably, pressure-sensing mechanism 101 is integrated into or onto an internal or external interface of membrane 110 itself, as long as chemical and puncture damage can be avoided for pressure-sensing mechanism 101.

FIG. 2 shows an alternative preferred embodiment in a partial side cross-section. Conventional tubular endorectal ultrasound imaging probe 203 has strain relief 204 and connecting cable 205. An ultrasound imaging transducer array 206 is situated near the tip of the probe for outward acoustic imaging into the adjacent prostate structure (not shown). Such imaging may be done on multiple image planes intersecting the indicated z-axis along different radii "R" by rotating probe 203 about the azimuthal z-axis. Additionally, probe 203 may be translated along the z-axis. Two pressure-sensing arrays 201 are shown peripherally and individually placed on each long azimuthal side of ultrasound imaging transducer array 206. Each pressure-sensing array 201 has pressure mapping pixels, each having a length 211 along the z axis. Optionally, the pressure reading at a given z axis position may be the average of two corresponding pressure pixels on either side of ultrasound imaging transducer array 206, or alternatively, the pressure-sensing arrays act as redundant backups for each other. A spatial and/or orientation position sensing mechanism is also shown as sensing mechanism 212 near the handle end of probe 203. Inflatable balloon or sock 213 is also shown by dotted lines. Although such balloons or socks keep the probe 203 clean in the prior art, they are not normally inflated to displace tissue for the rectal exam. An inflation tube 214 is shown routed to an inflation port inside the balloon 213. Inflation tube 214 is typically connected to a water or other liquid inflation or pressurization source outside the body (not shown).

The probe 203 of FIG. 2 may be used to determine body-tissue stiffness or mechanical properties knowing applied loading forces from the pressure-sensing mechanisms, and/or to provide an independent pressure map overlaid or presented with an ultrasound image. In the manner discussed earlier, the position or orientation sensing mechanism 212 may be utilized to record two or three dimensional positions and/or orientations relating to one or more samples of ultrasound image frames or pressure maps. As for FIG. 1, the mechanism(s) 201 comprise passive pressure sensors, active pressure sensors, or combined passive/active pressure sensing and pressure transmission mechanisms. An optional feature of probe 203 is the use of balloon 213. This balloon is used to perform calibrated loading and unloading of the prostate structures by alternatively applying and bleeding liquid (or gas) pressure from the interior of balloon 213. Under the influence of variable balloon 213 loading of body-tissue, the prostate may be observed in either the first or second embodiments. In the second embodiment, the pressure-sensing mechanisms 201 would record the settling of the body-tissues back against probe body 203 as the balloon 213 is collapsed. Any cancerous nodule or hard lump has its pressure peak amplified during such induced tissue motions, as opposed to having the body-tissue statically placed against the probe face. The balloon inflation feature may also be used to distort the prostate such that the prostate can be imaged in two different states of distortion in order to compute the widely quoted tissue shear-modulus, for example. The imposed liquid pressure, which is controlled, provides a known and reproducible state of loading for which induced distortions are imaged. The benefit of the balloon 213 is that this loading is done reproducibly from exam to exam and from patient to patient. In the manner of the previously discussed embodiment with a water-filled balloon, the probe may use ultrasound imaging and the known applied pressure to determine body-tissue properties. Probe 203 may also be used without balloon 213 in a manual palpation manner wherein the pressure-sensing mechanisms 201 operate in a passive or active mode.

FIG. 3 shows an alternative preferred embodiment of the invention. FIG. 3 is operationally similar to the probe shown in FIG. 2, except that the probe is modified for an external breast application. Probe 303 has strain relief 304 and connecting cable 305. Probe 303 has ultrasound imaging transducer array 306 and force or pressure mapping array sensing mechanism 301 shown situated along the middle of ultrasound imaging transducer array 306. This provides a centrally positioned force map in direct correspondence with the center of the ultrasound image slice thickness. Here, ultrasound imaging transducer array 306 has a piezoelement pitch of 311, while force array 306 has an element pitch shown approximately twice as large, with half the lineal density. Optionally, the force sensing (or application) mechanism array (or strip) may be situated on top of the piezomaterial (e.g., in the form of an aforementioned matching layer or window), in the piezomaterial (as shown), or under the piezomaterial. The preferred positions for the force sensing mechanism array are on top of, or in, or adjacent to, the ultrasound imaging transducer array 306.

The breast probe of FIG. 3 may image and sense forces or apply pressures in the manner of the first embodiment and/or the second embodiment. The shape of probe 303 is more suitable for use on the breast. A position or orientation sensing mechanism 312 is also shown again for the purpose of spatially addressing the image and/or force-map information.

The shown position or orientation sensing mechanisms 312a, 312b, and 312c may be magnetic positioners available from Polhemus Inc., located in Colchester, Vt., or Ascension Technology Corporation, located in South Burlington, Vt. Alternatively, one or more of the sensing mechanisms 312a, 312b, and 312c may be accelerometers or angle indicators.

Embodiments of the invention may include feedback or communication between the ultrasound imaging transducer arrays 106, 206, or 306 and the force or pressure-sensing (or application) mechanisms 101, 201, or 301. "Communication" can include, for example, co-presentation of pressure imaging results, or presentation of body-tissue stiffness as calculated from point-by-point loading versus displacement (or deformation). Feedback between the user and one or both of these sensing mechanisms may also be included. The force sensing (or application) mechanism may be linked to an audible, tactile, or visual feedback device, which prompts the user or operator to vary or control the applied force. The force sensing mechanism data may be used together with image-derived body-tissue distortion data to automatically calculate and map a shear-modulus of body-tissues in 2-D slices and/or 3-D volumes. The force or pressure-sensing mechanism 301 may be a normal force sensing mechanism or a shear-force sensing mechanism or a combination of both, and does not necessarily have to be an array, but might be a geometric arrangement of one or more force or pressure-sensing mechanisms of one or more types. The force or pressure-sensing mechanism measurements may also be noise-reduced by spatial or temporal averaging.

FIG. 4 is a perspective schematic view of one preferred probe configuration 400, with a secondary motion tracking transducer array image plane 402, and principal transducer array image plane 406, corresponding, respectively, to secondary transducer array 401 and principal transducer array 405. Probe configuration 400 also includes an active body-tissue palpation system, comprised of two exciters 408 and 410, which can be piezoelectric films, piezoelectric crystals, or other vibration driving means, such as electromagnetic voice-coil mechanisms. The active body-tissue palpation system is software or hardware controlled. Preferably, the operator controls the frequency of palpation vibration, the range of displacement, and the phasing between the palpation relative to the imaging. System cable 418 electronically connects the probe to the remainder of the ultrasound imaging system (not shown). Probe 400 is capable of acoustic imaging and controlled dynamic loading of the imaging field via transmission by exciters 408 and 410 of excitation vibrations. Such excitation vibrations may be in the few Hertz to MegaHertz range and may have controlled phase relationships and positional relationships with the imaging beams from 401 and 405. The excitation vibrations comprise single pulses, pulse trains, or pulse waveforms over extended periods of time, such as for a sine wave.

In one preferred embodiment, one or more force or pressure-sensing mechanisms are located near the imaging transducer arrays, and are attached to the face of the probe near principal transducer array 405. As principal transducer array 405 is drawn across body-tissue containing a structure of interest (e.g., skin tissue or a suspected tumor for removal), the surgeon observes the cross-section of the desired structure (e.g., the tumor 412) in transducer array plane 406 of principal transducer array 405. Different images may be acquired with the different transducer arrays 401 and 405. The different transducer arrays 401 and 405 are configured such that the azimuthal axis of secondary transducer array 401 is non-parallel to the azimuthal axis of principal transducer array 405. In one preferred embodiment, the azimuthal axis of secondary transducer array 401 is perpendicular to the azimuthal axis of principal transducer array 405 as shown in FIG. 4. The azimuthal and elevation axes are also shown for principal transducer array 405 and secondary transducer array 401, illustrating the relationship of these axes to an array. 2-D images can be selectively obtained from either the principal or secondary transducer arrays, -but preferably the secondary array is used primarily for motion tracking. Force or excitation applicators 408 and 410 may also have the ability to sense pseudostatic loading as caused by pressing of the probe 400 on the body as for the devices of FIGS. 1, 2, and 3. Thus, the probing forces may be manually applied by hand or dynamically applied by the system.

FIG. 5 is a side schematic view of one preferred construction of a transducer probe 500 contacting body-tissue 512. Transducer probe 500 comprises transducer housing 502, vibration applicators or exciters 508 and 510, and principal imaging transducer array 505, having an image plane 505a. Body-tissue 512 contains tumor 514, which is detected by the body-tissue palpation system of probe 500. Exciters 508 and 510 may conveniently be software-controlled. Preferably, the operator can control the frequency of palpation excitation, the depth of palpation, and the body-tissue palpation angle or direction relative to the imaging plane. For example, exciter 508 directs palpation (pressure) waves 508a into body-tissue 512 at velocity v. System cable 518 electronically connects the transducer probe 500 to the remainder of the ultrasound imaging system (not shown). The tumor 514 can be detected and correlated with the acoustic image by combining both the ultrasound imaging information and the sensed and/or known applied palpation forces (or their resulting distortions) vs. location. Such combinations can be via visual combination or a force map and an ultrasound image, by overlaying such images, or by presenting a body-tissue parameter map derived from the two sources of information.

Figure 6:
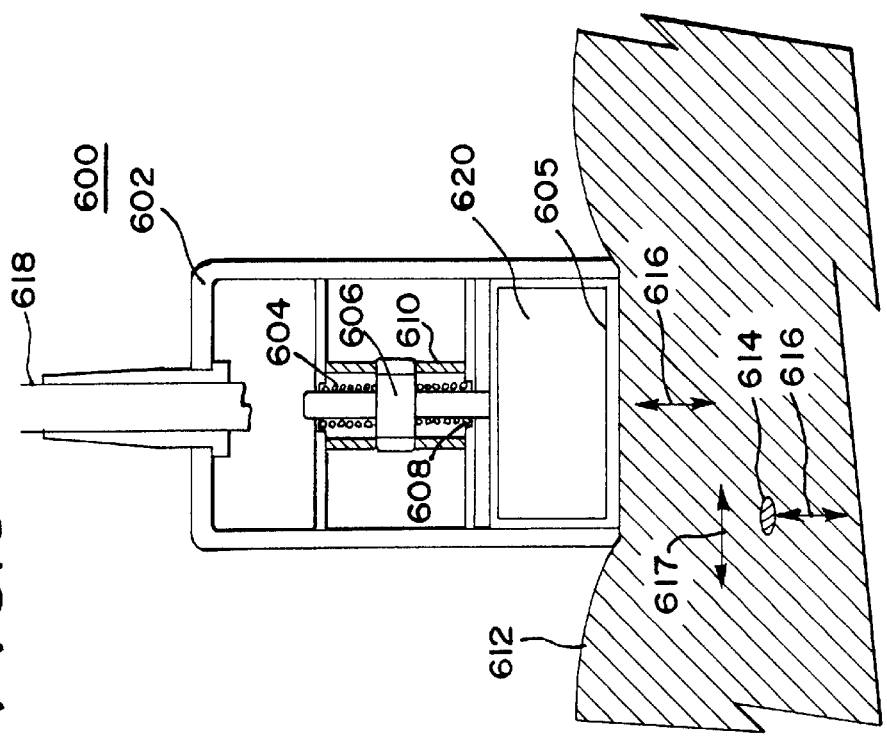
FIG. 6 is a side sectional view of another preferred construction of a linear body-tissue displacement transducer probe contacting body-tissue containing a tumor.

FIG. 6 is a schematic side view of another preferred construction of a transducer probe 600 contacting body-tissue 612. Transducer probe 600 comprises transducer housing 602, centering spring 604, solenoid actuator 606, solenoid coils 608 and 610, and ultrasound imaging array 605. Body-tissue 612 contains tumor 614, which is subject to vertical motion 616 from the body-tissue displacement system of probe 600. The body-tissue displacement system is comprised of solenoid actuator 606, backing block 620, ultrasound imaging array 605, and two solenoid coils 608 and 610, which are user-controlled by software or hardware circuits. Solenoid actuator 606, and thus backing block 620 and ultrasound imaging array 605, are activated or retracted in a vertical direction 616 by the relative amount of electrical current in solenoid coils 608 and 610. A strain gauge (not shown) is optionally attached to spring 604 to monitor the deployment of solenoid actuator 606 and imaging stack 620. System cable 618 electronically connects the transducer probe 600 to the remainder of the ultrasound imaging system (not shown).

Tissue near the center line of the transducer probe 600 can be expected to move towards and away, see 616, from the probe 600 while tissue away from the centerline can be expected to move laterally, see 617. Different neighboring tissue structures 614, when subject to mechanical displacements caused by an external apparatus 602, can be expected to move in a manner with respect to amplitude and phase determined by the mechanical properties of the tissue itself such as stiffness and density, as well as the way the structures are interconnected. Real time ultrasound images of the moving tissue structures can be used to observe the differences in the way neighboring structures move when subjected to external stresses. The experience of the diagnostician or software algorithms may be exploited to determine what is "normal" and what is not.

The Doppler capabilities of modern ultrasound imaging systems can further increase the apparent contrast between moving tissue structures because of the ability to depict different velocities, or different phrases, as different colors on the monitor.

Figure 7:
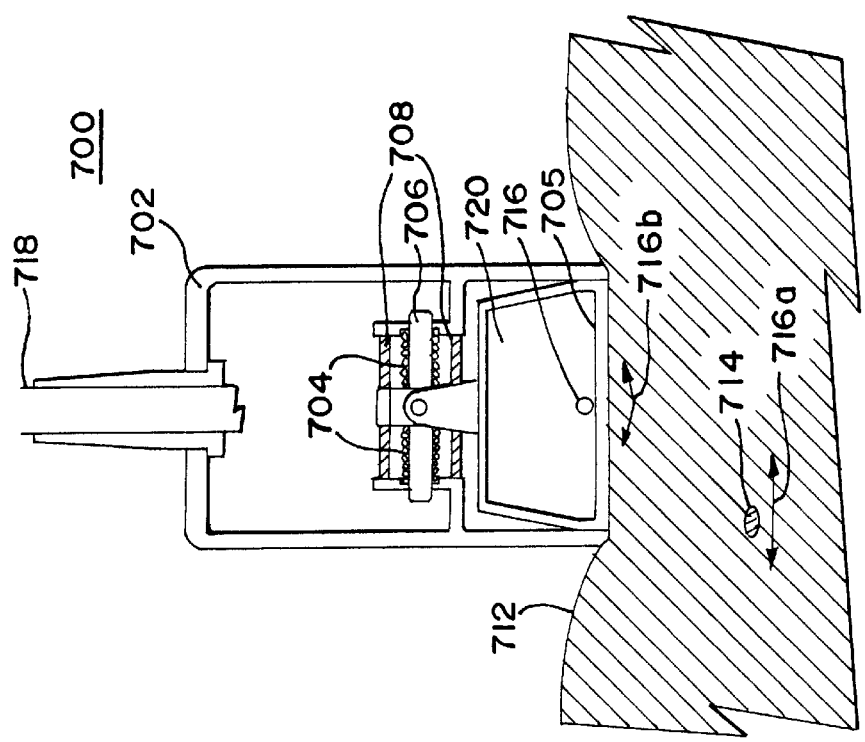
FIG. 7 is a side sectional view of another preferred configuration of a rotational body-tissue displacement transducer probe contacting body-tissue containing a tumor.

FIG. 7 is a sectional side view of another preferred configuration of a rotational body-tissue displacement transducer probe 700 contacting body-tissue 712 containing tumor 714. It applies motions 716a that are parallel to the probe face. Transducer probe 700 comprises transducer housing 702, centering springs 704, solenoid actuator 706, solenoid coils 708, backing block 720, and ultrasound imaging array 705. The body-tissue displacement system comprises two voice coils 708, solenoid actuator 706, and backing block 720, which are activated or retracted by the relative amount of electrical current in the solenoid coils 708. The electrical current is user-controlled by software. Preferably, the operator can control the frequency of actuation, the stroke of actuation, and the phasing between the ultrasound imaging and the rotation of backing block 720 (and thus body-tissue movement direction relative to the imaging plane) on pivot 716. The body-tissue displacement system, including ultrasound imaging array 705 and backing block 720, pivots in a rotational arc, see 716b, on pivot 716. Preferably, solenoid actuator 706 is retracted by spring 704 so that the body-tissue displacement mechanism is normally in a recessed position. In one embodiment of the invention, spring 704 is a small coil spring. System cable 718 electronically connects the transducer probe 700 to the remainder of the ultrasound imaging system (not shown).

FIG. 8 is a side and bottom view of an ultrasound transducer probe 800 with four force or pressure-sensing mechanisms and/or actuators 802, 804, 806, and 808 in transducer housing 810. The phasing of the mechanical excitation of exciters 802, 804, 806, and 808 are controlled to apply desired pressure or stress versus time at the body-tissue target locations. By altering the phase relationships between the exciters 802, 804, 806, and 808, body-tissue palpation in any direction can be achieved via phased beam-steering. Tissue can be moved within the imaging plane or be moved in and out of the imaging plane at pre-selected rates. Elastic body-tissue can be expected to have a highly damped resonance frequency that can be determined by a frequency sweep of the palpation exciters. The diagnostician adjusts and controls the relationship between the palpation excitation frequency and phase and the ultrasound frame rate to optimize the apparent contrast between tissue structures in the body being palpated by exciters 802, 804, 806, and 808.

A third embodiment involves the displacement of body-tissue in an ultrasound imaging field by muscle spasms induced by electrodes applying electrical pulses to selected areas of body-tissue. Preferably, a gel is applied to the skin that acoustically and electrically couples the ultrasound probe and electrodes to the tissue to be imaged. Elastic body-tissue can be expected to have a highly damped resonance frequency that can be determined by a frequency sweep of the electrode activation frequency. The relationship between the electrode actuation frequency and the ultrasound frame rate is expected to affect the imaging contrast between structures in the body being displaced by the electrodes.

FIG. 9 is a side and bottom view of an ultrasound transducer probe 900 with four electrodes for electrically-excited body-tissue displacement. Transducer probe 900 comprises electrodes 902, 904, 906, and 908 in transducer housing 910. Electrodes 902, 904, 906, and 908 are preferably independently controlled in both frequency and voltage. By altering the phase relationships between the electrodes, body-tissue displacement in any direction can be achieved, depending on the directionality of muscle spasms in response to applied electrical stimulation from the electrodes. The lateral displacement of body-tissue can be controlled by the amount of energy conveyed to the muscle tissue, since electrical current flowing through muscle tissue causes it to contract. The velocity of movement will reflect the temporal characteristics of the electrical stimulation. Probe 900 will image the net body-tissue displacement that occurs in the imaging plane 912 of ultrasound imaging array (not shown). The face of probe 900 is comprised of an acoustic lens material 914, typically silicone rubber, that laterally surrounds the electrodes and offers the advantages of a simpler transducer probe construction, a lighter transducer probe, operation without moving parts, and potentially less interference with ultrasound imaging by the transducer probe. Moreover, the effectiveness of the electrodes in producing body-tissue spasms may be greatly variable, depending on the relative amount of moisture/electrolyte and muscle tissue present in the particular body location and the condition of the body-tissue in proximity to the electrodes.

FIG. 10 is a side (profile) and bottom view of an ultrasound transducer probe accessory 1000 with four electrodes for electrical body-tissue displacement. Transducer probe accessory 1000 can be attached to a standard ultrasound transducer 1040 (shown in outline by dotted lines) using a latch assembly or by other means (e.g., attachment by a thumb screw). Transducer probe accessory 1000 comprises electrodes 1002, 1004, 1006, and 1008 in a housing 1010, with attachment screw 1020 and cable 1030 connected to a controller (not shown). Preferably, electrodes 1002, 1004, 1006, and 1008 are gold-plated and cooperatively controlled infrequency, voltage and phase A fourth embodiment involves a parameter measurement mechanism that measures the electrical impedance of a region of body-tissue in an ultrasound imaging filed of view. Electrical current flow is determined by the nature of the body-tissue and the characteristics of the electrical stimulation. Preferably, a gel is applied to the skin that acoustically and electrically couples the ultrasound probe and electrodes to the tissue to be imaged. By altering the phase relationships between the electrodes, electrical impedance measurement of body-tissue in any direction can be achieved in the acoustic imaging field, depending on the applied electrical stimulation from the electrodes. In this manner electrical impedance can be mapped in relation to acoustic image contrast. The preferred electrode configurations for measuring electrical impedance are similar to the electrode configurations preferred for electrical displacement of body-tissue, as shown in FIG. 9 and FIG. 10.

Alternative preferred embodiments with any of the previously discussed body-tissue parameter measurement mechanisms can incorporate any of several possible multiple transducer element configurations, as described in co-pending U.S. patent application Ser. No. 09/339,923, filed on Jun. 24, 1999, entitled "Intra-Operative Diagnostic Ultrasound Multiple-Array Transducer Probe and Optional Surgical Tool," which is assigned to the assignee of the present invention and hereby incorporated herein by reference.

Any type of ultrasound data can be used, alone or in combination. Specifically, for example, any of the following ultrasound imaging modalities may be used in accordance with the embodiments taught herein, with either fundamental or harmonic imaging or a combination thereof, either in the presence or in the absence of contrast agent: B-mode, Color Doppler Velocity, Color Doppler Energy, Color Doppler Variance, Doppler Tissue Velocity, Doppler Tissue Energy, Doppler Tissue Acceleration or any combination thereof. One preferred embodiment of the invention uses Doppler imaging as disclosed in copending U.S. patent application Ser. No. 08/736,895, filed Oct. 25, 1996, entitled "Imaging Modality Showing Energy and Velocity," which is assigned to the assignee of the present invention and hereby incorporated by reference.

Doppler velocity imaging allows an operator (e.g., a surgeon or sonographer) to help identify a tumor by its elastic resonant characteristic. When Doppler imaging is a primary interest, it is preferable to design the principal transducer array to form less than a 90 degree angle to the body-tissue movement of interest, so that a better Doppler signal is obtained.

3-D Imaging

The various multiple array ultrasound imaging probes described herein can be used for 3-D imaging as described in co-pending U.S. Pat. No. 6,014,473. A secondary transducer array can function as a tracking array for 3-D ultrasound image construction from a series of successive image planes obtained from sweeping a principal transducer array along the elevation axis (see FIG. 4). For 3-D imaging using principal and secondary ultrasound transducers, the principal and secondary imaging information needs to be provided concurrently, such that the secondary imaging information can be used to estimate the movement of the transducer probe and/or the body-tissue between respective image data frames.

Typically, these 3-D imaging capabilities are implemented by incorporating software routines for 3-D imaging. Hence, an ultrasound system desirably provides the capability for a surgeon or sonographer to easily switch the function of the secondary transducer array from providing images for 2-D imaging to tracking the motion of the principal transducer array. The ultrasound system could allow the surgeon or sonographer to select 2-D imaging or 3-D imaging by voice command, keyboard, foot pedal, or graphical user interface (e.g., mouse, trackball, touchpad, or other equivalent operator interfaces).

Figure 11:
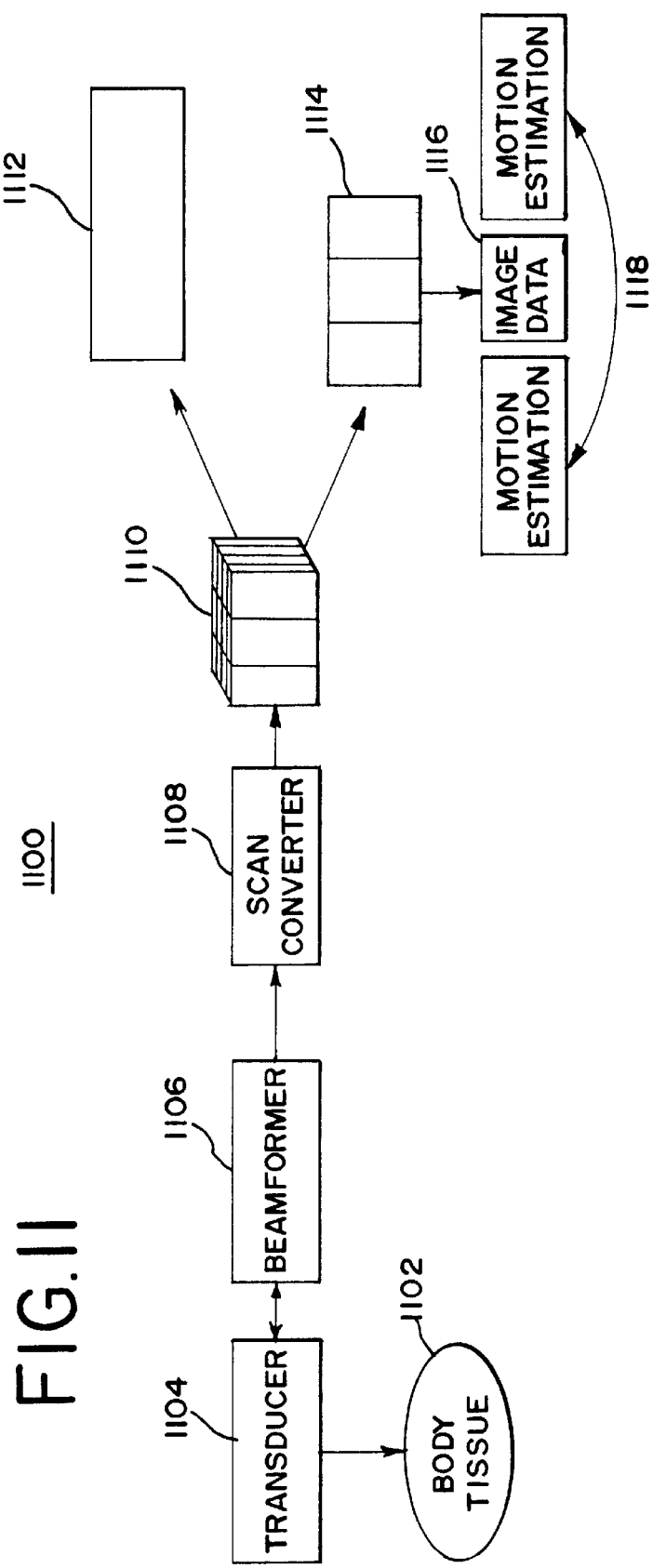
FIG. 11 shows how the ultrasound system can interpret the data obtained from a multiple transducer array probe and construct a 2-D display or a 3-D ultrasound display.

FIG. 11 shows how the ultrasound system may interpret the data obtained from a multiple array probe and construct a 2-D display or a 3-D display. In a 3-D display, a secondary array is used as a tracking array to provide motion estimation data as the principal transducer array is swept in the elevation direction. Transducer 1104 transmits pulses generated by system transmitters (not shown) to body tissue 1102, and receives echoes from interfaces in body tissue 1102. The signals to and from transducer 1104 are processed by beamformer 1106. Processed signals from beamformer 1106 are converted and presented to scan converter 1108 to produce data sets 1110. Data sets 1110 can be displayed as 2-D data 1112, or interpreted as 3-D data 1114, which are separated into image data 1116 and motion estimation data 1118 for 3-D image construction.

Plano-concave type arrays, e.g., as described in U.S. Pat. No. 5,415,175 to Hanafy et al., or 1.5-D type arrays (comprising a small number of element segments along the elevation direction of the array) can also be used as principal transducer arrays or secondary transducer arrays if required. Such arrays provide the capability of simulating a wider aperture 2-D ultrasound transducer array. Other types of arrays could also be used, e.g., annular arrays, linear, non-phased arrays, radial arrays or sector arrays, as described in U.S. Pat. No. 5,876,345 to Eaton et al.

Moreover, while PZT is preferred for fabricating the active ultrasound transducer elements, other materials, such as composite PZT and polyvinyldiene fluoride (PVDF) could be used. Single crystal grown transducers and capacitor micro-machined ultrasound transducers (cMUTs) could also be used as the active transducer elements.

Preferably, the embodiments incorporate reusable ultrasound imaging probes. If the ultrasound imaging probe is reusable, the probe is fabricated with plastic, which is tolerant of at least one application of chemical sterilization, steam sterilization (autoclaving), or Steris™ sterilization. Plastics that can be used for these embodiments include: Pellethane® thermoplastic polyurethane elastomer available from Dow Corporation, located in Midland, Mich., and Hytrel® polyester elastomer, available from Du Pont Corporation, located in Wilmington, Del.

The exemplary embodiments described herein are for purposes of illustration and are not intended to be limiting. Examples of variations within the scope of this invention include, but are not limited to, the following:

An attachable and even disposable probe accessory which can be attachable in various ways to provide a body-tissue parameter measurement mechanism to operate in conjunction with a conventional dedicated ultrasound transducer probe.

The probe can implement retracting mechanisms for the body-tissue manipulation or palpation tool or tools.

Sub-apertures of a 2-D transducer array can provide two or more transducer arrays at least one of which is used for motion tracking.

The selection of a 2-D imaging mode or a 3-D imaging mode by an operator would not preclude provision of a default imaging mode assumed by the medical ultrasound system.

Ultrasound information and body-tissue parameter information can be displayed simultaneously as 2-D images and 3-D images on one display device or on separate display devices.

A multiple array ultrasound imaging probe with a body-tissue parameter measurement mechanism can allow determination of the position of a tumor in body-tissue, and the information conveyed on a display could include icons, numeric or alphanumeric information, 2-D images, 3-D images, graphs or other graphical images, either in separate areas of the display or in colored overlays.

Moreover, one of skill in the art will appreciate that the diagrams are intended to be illustrative and not limiting. Specific details of implementation can be varied without departing from the scope of the invention. Many variations of ultrasound systems can be used in carrying out this invention. In fact, any commercial ultrasound platform can be used, including but not limited to: Acuson's Sequoia® and Aspen™ platforms; Philips/ATL's HDI® platforms; General Electric's LOGIQ™ platforms; Toshiba's PowerVision™ platforms; Hewlett-Packard's Sonos™ platforms; Siemen's Sonoline® and Elegra™ platforms; and the like. The instant invention does not depend on the specific type of ultrasound platform used, but rather, is directed to the manner in which ultrasound data is displayed with body-tissue parameter measurement data and to the co-integration of the ultrasound transducer and parameter measurement mechanisms.

Therefore, those skilled in the art will recognize that other embodiments could be practiced without departing from the scope and spirit of the claims set forth below.

What is claimed is:

1. A medical diagnostic ultrasound probe, comprising:
    one or more ultrasound imaging transducer elements for imaging a field of view within a body-tissue; and
    a body-tissue parameter measurement mechanism on the probe and being at least in part separate from the transducer elements for measuring a body-tissue parameter at least at one point in the field of view;
    wherein the body-tissue parameter measurement mechanism makes available at least one force, pressure, stress, or strain map or graph, in spatial and/or temporal relationship to at least one ultrasound image.

2. The probe of claim 1 wherein the body-tissue parameter mechanism applies a force, pressure, stress, or strain to a portion of body-tissue within the field of view of one or more ultrasound imaging transducer elements.

3. The probe of claim 2 wherein the force, pressure, stress, or strain varies temporally or spatially.

4. The probe of claim 1 wherein the body-tissue parameter mechanism obtains data for a force, pressure, stress, or strain map or graph, which is temporally interleaved with one or more ultrasound images.

5. The probe of claim 1 wherein the body-tissue parameter mechanism comprises at least one force, pressure, stress, or strain sensing mechanism which obtains data for a force, pressure, stress, or strain map or graph.

6. A medical diagnostic ultrasound probe, comprising:
    one or more ultrasound imaging transducer elements for imaging a field of view within a body-tissue; and
    a body-tissue parameter measurement mechanism on the probe and being at least in part separate from the transducer elements for measuring a body-tissue parameter at least at one point in the field of view;
    wherein the body-tissue parameter mechanism comprises at least one force, pressure, stress, or strain sensing mechanism which obtains data for a force, pressure, stress, or strain map or graph; and
    wherein the data is used to compute a body-tissue modulus.

7. The probe of claim 6 wherein the modulus is a shear modulus.

8. The probe of claim 1 wherein forces, pressures, stresses, or strains applied to body-tissue within the field of view of the ultrasound imaging transducer are due to: (a) mechanical manipulation of the probe by an operator's hand, and/or (b) mechanical or vibrational excitation generated by the body-tissue parameter measurement mechanism.

9. A medical diagnostic ultrasound probe, comprising:
    one or more ultrasound imaging transducer elements for imaging a field of view within a body-tissue; and
    a body-tissue parameter measurement mechanism on the probe and being at least in part separate from the transducer elements for measuring a body-tissue parameter at least at one point in the field of view;

wherein the body-tissue parameter measurement mechanism includes a plurality of electrodes.

10. The probe of claim 9, further comprising a body-tissue parameter measurement mechanism for measuring, or measuring data for computing, at least one body-tissue parameter.

11. A medical diagnostic ultrasound system for imaging body-tissue, comprising:

a principle ultrasound imaging transducer element with a field of view including body-tissue;

a secondary ultrasound imaging transducer element non-parallel to the principle ultrasound imaging transducer element;

a body-tissue parameter measurement mechanism for measuring, or measuring data for computing, at least one body-tissue parameter at least at one point in the field of view of the principal ultrasound imaging transducer element; and a display device to display ultrasound images in association with at least one measured or computed body-tissue parameter.

12. The system of claim 11 wherein the display device displays ultrasound images and at least one body-tissue parameter concerning body-tissue at least partly within the field of view of the principle ultrasound imaging transducer.

13. The system of claim 11 wherein the display device can selectively overlay or interleave at least one computed body-tissue parameter on at least one ultrasound image.

14. The system of claim 11 wherein the display device can display the spatial correlation of at least one measured or applied body-tissue parameter and an ultrasound image obtained by the principle ultrasound imaging transducer.

15. The system of claim 11 wherein the body-tissue parameter measurement mechanism applies at least one force, pressure, or stress, such as a normal, shear, compressional, rotational, or torsional force.

16. The system of claim 11 wherein the principal or secondary ultrasound imaging transducer provides acoustic imaging data for a 2-D image displayed on the display device.

17. The system of claim 11 wherein the principal ultrasound imaging transducer provides acoustic imaging data for a 3-D volume image displayed on the display device.

18. The system of claim 11 wherein the secondary ultrasound imaging transducer provides acoustic imaging data or positional data for a 3-D volume image displayed on the display device.

19. The system of claim 11 further comprising a linear array of body-tissue parameter measurement mechanisms.

20. The system of claim 11 further comprising one or more force or pressure-sensing or application mechanisms, wherein at least one body-tissue parameter measurement mechanism is located peripherally to the principal or secondary ultrasound imaging transducer.

21. The system of claim 11 further comprising one or more body-tissue parameter measurement mechanisms, wherein at least one body-tissue parameter measurement mechanism measures or manipulates body-tissue within the field of view of the principal or secondary ultrasound imaging transducer.

22. The system of claim 11 further comprising one or more body-tissue parameter measurement mechanisms, wherein at least one body-tissue parameter measurement mechanism includes a piezoelectric or piezoresistive material.

23. The system of claim 11 further comprising one or more body-tissue parameter measurement mechanisms including means for directing time-varying pressure or stress waves into the body-tissue.

24. The system of claim 11 further comprising one or more body-tissue parameter measurement mechanisms, wherein at least one body-tissue parameter measurement mechanism is attachable to an ultrasound imaging probe.

25. A method for using an ultrasound imaging transducer with a body-tissue parameter measurement mechanism, comprising:

imaging ultrasound images with an ultrasound imaging transducer; and measuring body-tissue parameter information with a body-tissue parameter measurement mechanism, the body-tissue parameter information derived from data free of acoustic echo information;

wherein imaging includes Doppler imaging.

26. A method for using an ultrasound imaging transducer with a body-tissue parameter measurement mechanism, comprising:

imaging ultrasound images with an ultrasound imaging transducer; and measuring body-tissue parameter information with a body-tissue parameter measurement mechanism, the body-tissue parameter information derived from data free of acoustic echo information;

wherein imaging includes imaging body tissue movement in and out of a field of view of the ultrasound imaging transducer.

27. The method of claim 25 wherein measuring body-tissue includes pressure or force sensing.

28. The method of claim 25 wherein measuring body-tissue includes mechanically displacing body-tissue.

29. A method for using an ultrasound imaging transducer with a body-tissue parameter measurement mechanism, comprising:

imaging ultrasound images with an ultrasound imaging transducer; and measuring body-tissue parameter information with a body-tissue parameter measurement mechanism, the body-tissue parameter information derived from data free of acoustic echo information;

wherein measuring body-tissue includes displacing body-tissue by electric stimulation of body-tissue by one or more electrodes.

30. A method for using an ultrasound imaging transducer with a body-tissue parameter measurement mechanism, comprising:

imaging ultrasound images with an ultrasound imaging transducer; and measuring body-tissue parameter information with a body-tissue parameter measurement mechanism, the body-tissue parameter information derived from data free of acoustic echo information;

wherein measuring body-tissue includes measuring an electrical impedance of body-tissue by a plurality of electrodes.

31. A method for operating a combined ultrasound imaging transducer and body-tissue parameter measurement system, comprising:

activating a plurality of body-tissue parameter measurement mechanisms integrated with a probe; and acoustically imaging a portion of body-tissue in a field of view of an ultrasound imaging transducer integrated with the probe adjacent to the plurality of body-tissue parameter measurement mechanisms, said portion under an influence of at least one of said mechanisms.

32. The method of claim 31 wherein activating the plurality of body-tissue parameter measurement mechanisms includes controlling a phase of at least one of said mechanisms.

33. The method of claim 31 wherein activating the plurality of body-tissue parameter measurement mechanisms includes controlling a frequency of activation.

34. The method of claim 31 wherein activating the plurality of body-tissue parameter measurement mechanisms includes controlling a sensitivity of their measurement range.

35. The method of claim 31 wherein activating the plurality of body-tissue parameter measurement mechanisms includes controlling an activation in relation to body-tissue imaged by the ultrasound imaging transducer.

36. The method of claim 31 wherein activating the plurality of body-tissue parameter measurement mechanisms includes independently controlling an activation frequency of a plurality of electrodes.

37. The method of claim 31 wherein activating the plurality of body-tissue parameter measurement mechanisms includes independently controlling at least one measurement range of the plurality of body-tissue parameter measurement mechanisms.

38. The method of claim 31 wherein activating the plurality of body-tissue parameter measurement mechanisms includes controlling activation of the plurality of body-tissue parameter measurement mechanisms for either rotational, torsional or shear displacement of body-tissue.

39. The method of claim 31 wherein imaging body-tissue includes Doppler imaging.

40. The method of claim 31 wherein activating a plurality of body-tissue parameter measurement mechanisms includes palpating a portion of the body-tissue in a field of view of the ultrasound imaging transducer.

41. An ultrasound imaging transducer assembly, comprising:

an ultrasound imaging transducer; and at least one body-tissue parameter measurement mechanism different from and coupled to the imaging transducer to measure body-tissue in coupled contact with the imaging transducer.

42. The ultrasound imaging transducer assembly of claim 41 wherein the body-tissue parameter measurement mechanism is a PVDF piezoelectric film.

43. The ultrasound imaging transducer assembly of claim 41 wherein the body-tissue parameter measurement mechanism is fabricated from a piezoelectric or piezoresistive material.

44. The ultrasound imaging transducer assembly of claim 41 wherein the body-tissue parameter measurement mechanism is responsive to software, firmware or electronic commands.

45. The ultrasound imaging transducer assembly of claim 41 further comprising means to control the body-tissue parameter measurement mechanism in relation to the imaging of the ultrasound imaging transducer.

46. The ultrasound imaging transducer assembly of claim 41 wherein the body-tissue parameter measurement mechanism contributes to a measurement of rotational, torsional, or shear displacement of body-tissue.

47. The ultrasound imaging transducer assembly of claim 41 further comprising means for measuring forces, pressures, or stresses in body-tissue.

48. The ultrasound imaging transducer assembly of claim 41 further comprising means for mechanically displacing body-tissue.

49. The ultrasound imaging transducer assembly of claim 41 further comprising electrodes for electrically inducing a displacement of body-tissue.

50. The ultrasound imaging transducer assembly of claim 41 further comprising electrodes for electrically measuring body-tissue.

51. The ultrasound imaging transducer assembly of claim 41 wherein the ultrasound imaging assembly is comprised of a first part with the ultrasound imaging transducer, and a detachable second part with a plurality of electrodes.

* * * * *